(12) United States Patent
de Villiers et al.

(10) Patent No.: US 9,402,745 B2
(45) Date of Patent: Aug. 2, 2016

(54) INTERVERTEBRAL PROSTHESIS PLACEMENT INSTRUMENT

(75) Inventors: Malan de Villiers, Wapadrand (ZA);
Ulrich Reinhard Hahnle, Saxonwold (ZA)

(73) Assignee: Simplify Medical, Inc., Sunnyvale, CA (US)

( * ) Notice: Subject to any disclaimer, the term of this patent is extended or adjusted under 35 U.S.C. 154(b) by 0 days.

(21) Appl. No.: 12/624,631

(22) Filed: Nov. 24, 2009

(65) Prior Publication Data

US 2010/0069976 A1    Mar. 18, 2010

Related U.S. Application Data

(60) Division of application No. 11/187,403, filed on Jul. 21, 2005, which is a continuation of application No. PCT/IB2004/000170, filed on Jan. 26, 2004.

(30) Foreign Application Priority Data

Jan. 31, 2003   (ZA) ........................................ 03/0875

(51) Int. Cl.
*A61F 2/46*     (2006.01)
*A61F 2/44*     (2006.01)
(Continued)

(52) U.S. Cl.
CPC ............ *A61F 2/4657* (2013.01); *A61B 17/1757* (2013.01); *A61B 2090/3916* (2016.02); *A61F 2/44* (2013.01); *A61F 2002/3008* (2013.01); *A61F 2002/4658* (2013.01); *A61F 2250/0098* (2013.01)

(58) Field of Classification Search
CPC .................................................... A61B 17/1757
USPC ......................................................... 606/99, 90
See application file for complete search history.

(56) References Cited

U.S. PATENT DOCUMENTS

| 3,486,505 A | 12/1969 | Morrison |
| 3,867,728 A | 2/1975 | Stubstad et al. |
| 4,309,777 A | 1/1982 | Patil |

(Continued)

FOREIGN PATENT DOCUMENTS

| DE | 3023353 A1 | 4/1981 |
| DE | 10035182 A1 | 2/2002 |

(Continued)

OTHER PUBLICATIONS

Hellier et al., "Wear Studies for Development of an Intervertebral Disc Prosthesis," *Spine*, vol. 17 No. 6 Supplement pp. 86-96 (1992).

(Continued)

*Primary Examiner* — David Bates
(74) *Attorney, Agent, or Firm* — Wilson, Sonsini, Goodrich & Rosati

(57) ABSTRACT

The invention concerns an intervertebral prosthesis placement instrument which can be used to facilitate accurate positioning of a spinal disc prosthesis between adjacent spinal vertebrae. The instrument (10) has opposed jaws 12 formed with tips (24) that are shaped for insertion between the vertebrae. The jaws can be moved apart from one another to distract the vertebrae, allowing the prosthesis to enter between the vertebrae. The jaws also have opposed surfaces which are shaped to embrace the prosthesis between them and to guide the prosthesis into position.

10 Claims, 1 Drawing Sheet

(51) Int. Cl.
 *A61B 17/17* (2006.01)
 *A61F 2/30* (2006.01)

(56) References Cited

U.S. PATENT DOCUMENTS

| | | | |
|---|---|---|---|
| 4,531,917 A | 7/1985 | Linkow et al. | |
| 4,566,466 A | 1/1986 | Ripple et al. | |
| 4,619,660 A | 10/1986 | Christiansen et al. | |
| 4,673,407 A | 6/1987 | Martin | |
| 4,759,766 A | 7/1988 | Buettner-Janz et al. | |
| 4,759,769 A | 7/1988 | Hedman et al. | |
| 4,834,757 A | 5/1989 | Brantigan | |
| 4,863,477 A | 9/1989 | Monson | |
| 4,904,261 A | 2/1990 | Dove et al. | |
| 4,917,704 A | 4/1990 | Frey et al. | |
| 4,932,969 A | 6/1990 | Frey et al. | |
| 4,946,378 A * | 8/1990 | Hirayama et al. | 623/17.16 |
| 4,997,432 A * | 3/1991 | Keller | 623/17.11 |
| 5,035,716 A | 7/1991 | Downey | |
| 5,057,108 A | 10/1991 | Shetty et al. | |
| 5,071,437 A | 12/1991 | Steffee | |
| 5,122,130 A | 6/1992 | Keller | |
| 5,195,526 A | 3/1993 | Michelson | |
| 5,258,031 A | 11/1993 | Salib et al. | |
| 5,282,861 A | 2/1994 | Kaplan | |
| 5,314,477 A * | 5/1994 | Marnay | 623/17.15 |
| 5,320,644 A | 6/1994 | Baumgartner | |
| 5,370,697 A | 12/1994 | Baumgartner | |
| 5,394,457 A | 2/1995 | Leibinger et al. | |
| 5,401,269 A | 3/1995 | Buttner-Janz et al. | |
| 5,415,704 A | 5/1995 | Davidson | |
| 5,458,642 A | 10/1995 | Beer et al. | |
| 5,462,575 A | 10/1995 | Del Corso | |
| 5,484,437 A | 1/1996 | Michelson | |
| 5,489,307 A | 2/1996 | Kuslich et al. | |
| 5,505,732 A | 4/1996 | Michelson | |
| 5,507,816 A | 4/1996 | Bullivant | |
| 5,534,030 A | 7/1996 | Navarro et al. | |
| 5,556,431 A | 9/1996 | Buttner-Janz | |
| 5,571,109 A * | 11/1996 | Bertagnoli | A61B 17/025 606/86 A |
| 5,674,296 A | 10/1997 | Bryan et al. | |
| 5,676,701 A | 10/1997 | Yuan et al. | |
| 5,676,702 A | 10/1997 | Ratron | |
| 5,683,465 A | 11/1997 | Shinn et al. | |
| 5,702,450 A | 12/1997 | Bisserie | |
| 5,709,683 A | 1/1998 | Bagby | |
| 5,728,159 A | 3/1998 | Stroever et al. | |
| 5,741,253 A | 4/1998 | Michelson | |
| 5,776,198 A | 7/1998 | Rabbe et al. | |
| 5,782,832 A | 7/1998 | Larsen et al. | |
| 5,797,909 A | 8/1998 | Michelson | |
| 5,824,094 A | 10/1998 | Serhan et al. | |
| 5,836,948 A | 11/1998 | Zucherman et al. | |
| 5,865,846 A | 2/1999 | Bryan et al. | |
| 5,865,848 A | 2/1999 | Baker | |
| 5,888,226 A | 3/1999 | Rogozinski | |
| 5,895,428 A | 4/1999 | Berry | |
| 5,899,901 A | 5/1999 | Middleton | |
| 5,899,911 A | 5/1999 | Carter | |
| 5,928,284 A | 7/1999 | Mehdizadeh | |
| 5,989,251 A | 11/1999 | Nichols | |
| 5,989,291 A | 11/1999 | Ralph et al. | |
| 6,001,130 A | 12/1999 | Bryan et al. | |
| 6,019,792 A | 2/2000 | Cauthen | |
| 6,022,376 A | 2/2000 | Assell et al. | |
| 6,039,761 A | 3/2000 | Li et al. | |
| 6,039,763 A | 3/2000 | Shelokov | |
| 6,080,155 A | 6/2000 | Michelson | |
| 6,083,228 A | 7/2000 | Michelson | |
| 6,086,613 A | 7/2000 | Camino et al. | |
| 6,096,038 A | 8/2000 | Michelson | |
| 6,132,465 A | 10/2000 | Ray et al. | |
| 6,136,031 A | 10/2000 | Middleton | |
| 6,139,551 A | 10/2000 | Michelson et al. | |
| 6,139,579 A | 10/2000 | Steffee et al. | |
| 6,143,033 A | 11/2000 | Paul et al. | |
| 6,146,421 A | 11/2000 | Gordon et al. | |
| 6,156,067 A | 12/2000 | Bryan et al. | |
| 6,159,214 A | 12/2000 | Michelson | |
| 6,162,252 A | 12/2000 | Kuras et al. | |
| 6,174,311 B1 | 1/2001 | Branch et al. | |
| 6,176,881 B1 | 1/2001 | Schar et al. | |
| 6,193,757 B1 | 2/2001 | Foley et al. | |
| 6,224,595 B1 | 5/2001 | Michelson | |
| 6,224,607 B1 | 5/2001 | Michelson | |
| 6,231,609 B1 | 5/2001 | Mehdizadeh | |
| 6,235,030 B1 | 5/2001 | Zucherman et al. | |
| 6,241,769 B1 * | 6/2001 | Nicholson et al. | 623/17.11 |
| 6,261,296 B1 * | 7/2001 | Aebi | A61B 17/025 600/219 |
| 6,264,695 B1 | 7/2001 | Stoy | |
| 6,290,726 B1 | 9/2001 | Pope et al. | |
| 6,296,664 B1 | 10/2001 | Middleton | |
| 6,315,797 B1 | 11/2001 | Middleton | |
| 6,322,567 B1 | 11/2001 | Mittelstadt et al. | |
| 6,336,941 B1 | 1/2002 | Subba Rao et al. | |
| 6,348,071 B1 | 2/2002 | Steffee et al. | |
| 6,368,350 B1 | 4/2002 | Erickson et al. | |
| 6,368,351 B1 | 4/2002 | Glenn et al. | |
| 6,375,681 B1 | 4/2002 | Truscott | |
| 6,375,682 B1 | 4/2002 | Fleischmann et al. | |
| 6,395,032 B1 | 5/2002 | Gauchet | |
| 6,402,785 B1 | 6/2002 | Zdeblick et al. | |
| 6,409,766 B1 | 6/2002 | Brett | |
| 6,413,278 B1 | 7/2002 | Marchosky | |
| 6,416,551 B1 | 7/2002 | Keller | |
| 6,436,098 B1 | 8/2002 | Michelson | |
| 6,440,139 B2 | 8/2002 | Michelson | |
| 6,447,544 B1 | 9/2002 | Michelson | |
| 6,478,800 B1 | 11/2002 | Fraser et al. | |
| 6,517,544 B1 | 2/2003 | Michelson | |
| 6,517,580 B1 | 2/2003 | Ramadan et al. | |
| 6,520,967 B1 | 2/2003 | Cauthen | |
| 6,520,996 B1 | 2/2003 | Manasas et al. | |
| 6,527,804 B1 | 3/2003 | Gauchet et al. | |
| 6,533,817 B1 | 3/2003 | Norton et al. | |
| 6,537,279 B1 | 3/2003 | Michelson | |
| 6,554,863 B2 | 4/2003 | Paul et al. | |
| 6,562,047 B2 | 5/2003 | Ralph et al. | |
| 6,562,074 B2 | 5/2003 | Gerbec et al. | |
| 6,565,574 B2 | 5/2003 | Michelson | |
| 6,582,466 B1 | 6/2003 | Gauchet | |
| 6,582,468 B1 | 6/2003 | Gauchet | |
| 6,592,624 B1 | 7/2003 | Fraser et al. | |
| 6,599,294 B2 * | 7/2003 | Fuss et al. | 606/99 |
| 6,607,558 B2 | 8/2003 | Karus | |
| 6,607,559 B2 | 8/2003 | Ralph et al. | |
| 6,610,092 B2 | 8/2003 | Ralph et al. | |
| 6,623,525 B2 | 9/2003 | Ralph et al. | |
| 6,645,248 B2 | 11/2003 | Casutt | |
| 6,648,895 B2 | 11/2003 | Burkus et al. | |
| 6,652,533 B2 | 11/2003 | O'Neil | |
| 6,660,038 B2 | 12/2003 | Boyer, II et al. | |
| 6,666,866 B2 | 12/2003 | Martz et al. | |
| 6,669,731 B2 | 12/2003 | Ralph et al. | |
| 6,669,732 B2 | 12/2003 | Serhan et al. | |
| 6,673,113 B2 | 1/2004 | Ralph et al. | |
| 6,682,562 B2 | 1/2004 | Viart et al. | |
| 6,689,132 B2 | 2/2004 | Biscup | |
| 6,706,068 B2 | 3/2004 | Ferree | |
| 6,709,439 B2 | 3/2004 | Rogers et al. | |
| 6,712,819 B2 | 3/2004 | Zucherman et al. | |
| 6,712,825 B2 | 3/2004 | Aebi et al. | |
| 6,723,097 B2 | 4/2004 | Fraser et al. | |
| 6,726,720 B2 | 4/2004 | Ross et al. | |
| 6,726,721 B2 | 4/2004 | Stoy et al. | |
| 6,733,532 B1 | 5/2004 | Gauchet et al. | |
| 6,740,118 B2 * | 5/2004 | Eisermann et al. | 623/17.14 |
| 6,740,119 B2 | 5/2004 | Errico et al. | |
| 6,755,841 B2 | 6/2004 | Fraser et al. | |
| 6,764,512 B2 | 7/2004 | Keller | |
| 6,764,515 B2 | 7/2004 | Ralph et al. | |
| 6,770,095 B2 | 8/2004 | Grinberg et al. | |

(56) References Cited

U.S. PATENT DOCUMENTS

| | | |
|---|---|---|
| 6,790,233 B2 | 9/2004 | Brodke et al. |
| 6,793,678 B2 | 9/2004 | Hawkins |
| 6,814,737 B2 | 11/2004 | Cauthen |
| 6,821,298 B1 | 11/2004 | Jackson |
| 6,827,740 B1 | 12/2004 | Michelson |
| 6,830,570 B1 | 12/2004 | Frey et al. |
| 6,846,328 B2 | 1/2005 | Cauthen |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,649 B2 | 8/2006 | Zucherman et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,583 B1 | 12/2007 | Schar et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | de Villiers et al. |
| 7,452,380 B2 | 11/2008 | Zubok et al. |
| 7,491,241 B2 | 2/2009 | Errico et al. |
| 7,494,508 B2 | 2/2009 | Zeegers |
| 7,531,001 B2 | 5/2009 | de Villiers et al. |
| 7,637,913 B2 | 12/2009 | De Villiers et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0049497 A1 * | 4/2002 | Mason ................. 623/17.11 |
| 2002/0068936 A1 | 6/2002 | Burkus et al. |
| 2002/0091392 A1 | 7/2002 | Michelson |
| 2002/0116009 A1 * | 8/2002 | Fraser ................. A61F 2/4611 606/99 |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree et al. |
| 2003/0083747 A1 | 5/2003 | Winterbottom et al. |
| 2003/0100951 A1 | 5/2003 | Serhan et al. |
| 2003/0125739 A1 | 7/2003 | Bagga |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233155 A1 | 12/2003 | Landry et al. |
| 2004/0002761 A1 | 1/2004 | Rogers et al. |
| 2004/0024407 A1 | 2/2004 | Ralph et al. |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | de Villiers et al. |
| 2005/0021146 A1 | 1/2005 | de Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0055098 A1 * | 3/2005 | Zdeblick ............ A61B 17/1671 623/17.11 |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0192586 A1 | 9/2005 | Zucherman et al. |
| 2005/0192670 A1 | 9/2005 | Zubok et al. |
| 2005/0197706 A1 | 9/2005 | Hovorka et al. |
| 2005/0216081 A1 | 9/2005 | Taylor |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0251262 A1 | 11/2005 | de Villiers et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |
| 2006/0020342 A1 | 1/2006 | Ferree et al. |

(56) References Cited

U.S. PATENT DOCUMENTS

| | | |
|---|---|---|
| 2006/0025862 A1 | 2/2006 | de Villiers et al. |
| 2006/0029186 A1 | 2/2006 | de Villiers et al. |
| 2006/0030857 A1 | 2/2006 | de Villiers et al. |
| 2006/0030862 A1 | 2/2006 | de Villiers et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Feree |
| 2006/0069439 A1 | 3/2006 | Zucherman et al. |
| 2006/0142858 A1 | 6/2006 | Colleran |
| 2006/0142862 A1 | 6/2006 | Diaz et al. |
| 2006/0155378 A1 | 7/2006 | Eckman |
| 2006/0167549 A1 | 7/2006 | Mathys et al. |
| 2006/0178744 A1 | 8/2006 | de Villiers et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0293752 A1 | 12/2006 | Moumene et al. |
| 2006/0293754 A1 | 12/2006 | de Villiers et al. |
| 2007/0010826 A1 | 1/2007 | Rhoda et al. |
| 2007/0021837 A1 | 1/2007 | Ashman |
| 2007/0032875 A1 | 2/2007 | Blacklock et al. |
| 2007/0061011 A1 | 3/2007 | de Villiers et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168036 A1 | 7/2007 | Ainsworth et al. |
| 2007/0179615 A1 | 8/2007 | Heinz et al. |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270970 A1 | 11/2007 | Trieu |
| 2007/0282449 A1 | 12/2007 | de Villiers et al. |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | de Villiers et al. |
| 2008/0051901 A1 | 2/2008 | de Villiers et al. |
| 2008/0125864 A1 | 5/2008 | de Villiers et al. |
| 2008/0133011 A1 | 6/2008 | de Villiers et al. |
| 2008/0154301 A1 | 6/2008 | de Villiers et al. |
| 2008/0154382 A1 | 6/2008 | de Villiers et al. |
| 2008/0215155 A1 | 9/2008 | de Villiers et al. |
| 2008/0221696 A1 | 9/2008 | de Villiers et al. |
| 2008/0228274 A1 | 9/2008 | de Villiers et al. |
| 2008/0228277 A1 | 9/2008 | de Villiers et al. |
| 2008/0294259 A1 | 11/2008 | de Villiers et al. |
| 2009/0043391 A1 | 2/2009 | de Villiers et al. |
| 2009/0048674 A1 | 2/2009 | Zubok et al. |
| 2009/0048677 A1 | 2/2009 | McLeod et al. |
| 2009/0076614 A1 | 3/2009 | Arramon |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0222101 A1 | 9/2009 | de Villiers et al. |
| 2009/0276051 A1 | 11/2009 | Arramon et al. |
| 2010/0004746 A1 | 1/2010 | Arramon |
| 2010/0016972 A1 | 1/2010 | Jansen et al. |
| 2010/0016973 A1 | 1/2010 | de Villiers et al. |
| 2010/0049040 A1 | 2/2010 | de Villiers et al. |

FOREIGN PATENT DOCUMENTS

| | | |
|---|---|---|
| EP | 0 333 990 A2 | 9/1989 |
| EP | 0333990 A3 | 5/1990 |
| EP | 0 560 140 A1 | 9/1993 |
| EP | 0 560 141 A1 | 9/1993 |
| EP | 0 591 712 A1 | 4/1994 |
| EP | 0 820 740 | 1/1998 |
| EP | 1 142 544 A1 | 10/2001 |
| EP | 1 153 582 A2 | 11/2001 |
| EP | 1153582 A3 | 11/2001 |
| EP | 1 250 898 A1 | 10/2002 |
| EP | 1 306 064 A1 | 5/2003 |
| EP | 1 344 493 A1 | 9/2003 |
| EP | 1 344 506 A1 | 9/2003 |
| EP | 1 344 507 A2 | 9/2003 |
| EP | 1 344 508 A3 | 9/2003 |
| EP | 1 405 615 A1 | 4/2004 |
| EP | 1 417 940 A1 | 5/2004 |
| EP | 1 570 813 | 9/2005 |
| FR | 2 803 741 | 7/2001 |
| JP | 61-122859 | 6/1986 |
| JP | 63-164948 | 7/1988 |
| JP | 01-136655 | 5/1989 |
| JP | 06-007391 | 1/1994 |
| JP | 2002-521090 T | 7/2002 |
| JP | 2003-508119 T | 3/2003 |
| WO | WO 99/20209 | 4/1999 |
| WO | WO 99/30651 | 6/1999 |
| WO | WO 00/04851 | 2/2000 |
| WO | WO 00/35384 | 6/2000 |
| WO | WO 00/42954 | 7/2000 |
| WO | WO 00/42954 A3 | 11/2000 |
| WO | WO 01/01893 A1 | 1/2001 |
| WO | WO 01/15637 | 3/2001 |
| WO | WO 01/28468 A1 | 4/2001 |
| WO | WO 01/68003 A1 | 9/2001 |
| WO | WO 02/11650 | 2/2002 |
| WO | WO 04/000170 | 12/2003 |
| WO | WO 04/000171 | 12/2003 |
| WO | WO 2004/026187 A1 | 4/2004 |
| WO | WO 2004/054477 | 7/2004 |
| WO | WO 2005/004756 A2 | 1/2005 |
| WO | WO 2005/004756 A3 | 1/2005 |
| WO | WO 2005/053580 A1 | 6/2005 |
| WO | WO 2005/072662 | 8/2005 |
| WO | WO 2005/112834 | 12/2005 |
| WO | WO 2005/112834 A3 | 5/2006 |
| WO | WO 2006/119092 A2 | 11/2006 |
| WO | WO 2006/119092 A3 | 11/2006 |
| WO | WO 2007/121320 | 10/2007 |
| WO | WO 2007/121320 A3 | 6/2008 |
| ZA | 03/9312 | 11/2003 |

OTHER PUBLICATIONS

Lee et al., "Impact Response of the Intervertebral Disc in a Finite-Element Model," *Spine* vol. 25, No. 19, pp. 2431-2439 (2000).

Lehuec et al., "Shock Absorption in Lumber Disc Prosthesis," *Journal of Spinal Disorders & Techniques,* vol. 16, No. 4, pp. 346-351(2003).

International search report and written opinion dated Jun. 4, 2004 for PCT/IB2004/000171.

"Notice of allowance dated Nov. 7, 2013 for U.S. Appl. No. 11/187,403."

"Office action dated Jan. 21, 2010 for U.S. Appl. No. 11/187,403."

"Office action dated Mar. 19, 2009 for U.S. Appl. No. 11/187,403."

"Office action dated Jul. 21, 2010 for U.S. Appl. No. 11/187,403."

"Office action dated Sep. 16, 2009 for U.S. Appl. No. 11/187,403."

\* cited by examiner

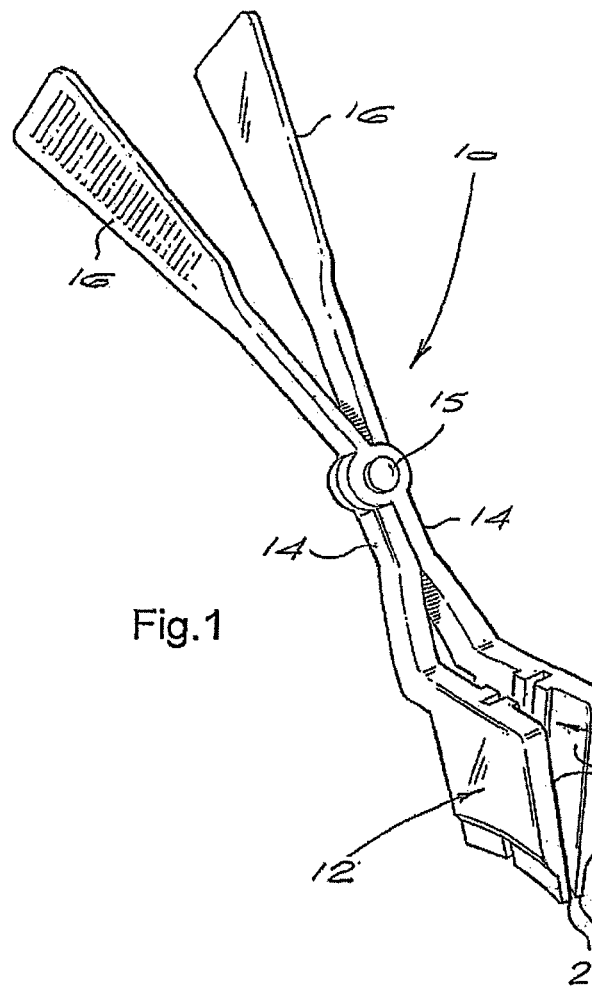
Fig.1
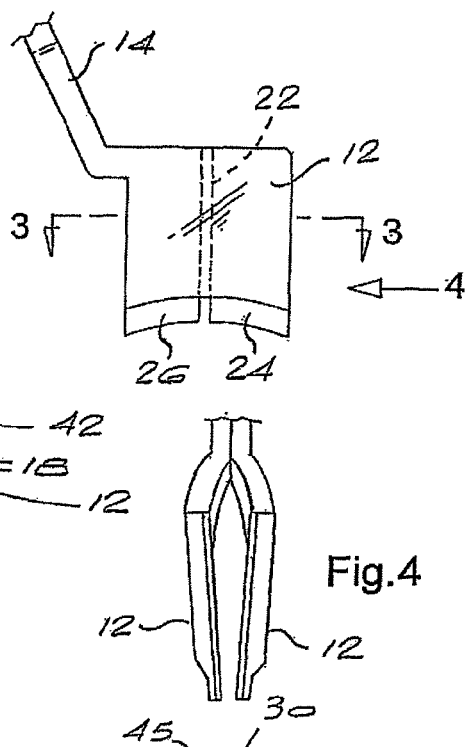
Fig.2
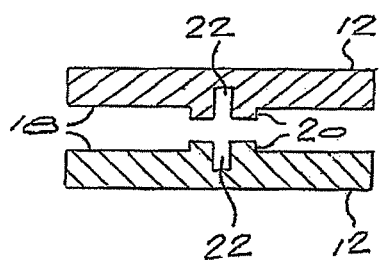
Fig.3
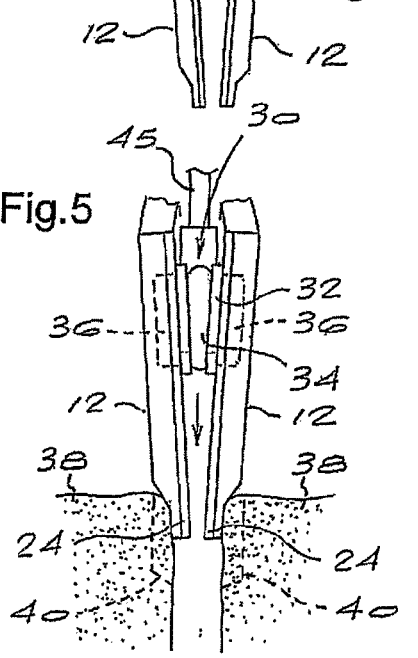
Fig.4
Fig.5

INTERVERTEBRAL PROSTHESIS PLACEMENT INSTRUMENT

CROSS-REFERENCES TO RELATED APPLICATIONS

The present application is a Divisional of U.S. patent application. Ser. No. 11/187,403 filed on Jul. 21, 2005, which application is a continuation of International Application No. PCT/IB2004/000170 filed on Jan. 26, 2004, which claimed priority from South African application 2003/0875 filed on Jan. 31, 2003; the full disclosures, all of which are incorporated herein by reference.

BACKGROUND OF THE INVENTION

This invention relates to an intervertebral prosthesis placement instrument.

Various types of intervertebral prosthesis are known. Examples are that marketed by Waldemar Link GmbH & Co under the trade mark LINK SB Charité™ and those described in EP 0 560 140, EP 0 560 141 (both Waldemar Link GmbH & Co) and ZA 2002/7517.

It is an object of the present invention to provide an instrument which can be used to place an intervertebral prosthesis, such as one of those mentioned above, in an intervertebral space.

BRIEF SUMMARY OF THE INVENTION

According to the present invention there is provided an intervertebral prosthesis placement instrument comprising opposed jaws having tips shaped for insertion between adjacent vertebrae between which the prosthesis is to be placed, the jaws being movable apart from one another to cause distraction of the vertebrae and having opposing surfaces shaped to embrace the prosthesis between them and to guide the prosthesis into position between the distracted vertebrae.

In the preferred embodiment, the tips of the jaws are relatively sharp in relation to remaining portions of the jaws, thereby enabling the tips to be inserted between the vertebrae prior to distraction. The opposing surfaces of the jaws may include slots in which fins carried by the prosthesis and projecting in opposite directions are slidably receivable, the slots serving in use to guide the fins into opposing slots formed in the vertebrae.

The jaws may be carried by a scissors, forceps or tongs type mechanism having handles operable to move the jaws apart from one another. Preferably the jaws are inclined relative to one another and the handles are inclined relative to the slots, these features allowing the prosthesis to be inserted initially between the jaws.

The jaws may, for instance, inclined towards one another in a direction towards their tips with the maximum spacing between the jaws at positions remote from the tips being sufficient for the prosthesis to be inserted between the jaws.

Further according to the invention there is provided the combination of an instrument as summarized above and a tool which is operable to drive the prosthesis through the jaws and into position between the vertebrae:

Other features of the invention are set forth in the appended claims.

BRIEF DESCRIPTION OF THE DRAWINGS

The invention will now be described in more detail, by way of example only, with reference to the accompanying drawings in which:

FIG. 1 shows a perspective view of an instrument according to this invention;

FIG. 2 shows a side view of a portion of the instrument seen in FIG. 1;

FIG. 3 shows a cross-section at the line 3-3 in FIG. 2;

FIG. 4 shows a view of the instrument in the direction of the arrow 4 in FIG. 2; and FIG. 5 shows the instrument in use.

DETAILED DESCRIPTION OF THE INVENTION

The illustrated intervertebral prosthesis placement instrument 10 has a pair of jaws 12 carried by arms 14 which form part of a scissor-type mechanism having a single hinge point 15 and which are provided with handles 16 at their ends remote from the jaws. The jaws have opposing surfaces 18 formed with inwardly projecting ribs 20 and transverse slots 22 which extend for the height of the jaws as viewed in FIG. 2. At their free ends the jaws 12 are provided with relatively sharp tips or blades 24 having curved extremities 26.

As will be apparent from FIGS. 1 and 2, the arms 14 are inclined relative to the jaws. It will be understood that by appropriate manipulation of the handles 16, in the illustrated case by moving them apart from one another, will serve to pivot the jaws apart from one another. The invention also envisages embodiments in which a double hinge arrangement is provided whereby movement of the handles towards one another will pivot the jaws apart from one another.

Reference is made, by way of example only, to the specification of applicant's international patent application PCT/IB03/04051 which describes an intervertebral prosthesis having opposing plates located on opposite sides of a central core on which the plates can articulate. The plates have projecting fins which, during placement of the prosthesis, locate in slots created for the purpose in opposing surfaces of adjacent vertebra between which the prosthesis is to be installed.

The instrument illustrated in FIGS. 1 to 4 is designed for use in placement of such a prosthesis. The prosthesis is indicated in FIG. 5 by the numeral 30. The abovementioned plates are indicated by the numeral 32, the core by the numeral 34 and the fins by the numeral 36.

FIG. 5 also shows portions of two adjacent vertebra 38 in which saw cuts have been made to form the slots 40 which will receive the fins.

In order to place the prosthesis 30 it is necessary to distract the vertebra, i.e separate them by a distance sufficient for entry of the prosthesis between them. To achieve this the tips 24 of the jaws 12 are inserted between the vertebra with the slots 22 in the jaws aligned with the slots 40. The handles 14 may then be manipulated to force the jaws, and hence the vertebrae, apart from one another. The prosthesis 30 is then slipped into the gap between the jaws so as to be embraced therein with the fins 36 in the slots 22. The prosthesis is then slipped downwardly through the inter-jaw gap. Throughout this movement the prosthesis is guided by the guidance of the fins 36 in the slots 22. The prosthesis is moved right through the inter-jaw gap and eventually past the tips 24 so as to locate between the vertebrae with the fins in the slots 40.

It will accordingly be understood that the slots 22 serve to guide the fins into the slots 40.

Referring to FIG. 4 it will be noted that the jaws are inclined towards one another in a direction towards their tips 24. The gap 42 between them at the top, i.e. at their extremities remote from the tips 24, is sufficient for initial insertion of the prosthesis between them at this location. Thus in an alternative placement procedure it is possible to locate the prosthesis initially in the gap 42 and then drive it downwardly so as to force the jaws, and hence the vertebrae, apart from one another instead of manipulating the handles to force the jaws apart. The numeral 44 in FIG. 5 indicates a tool which is used to hold and position the prosthesis during the placement procedure. It will be possible to tap on the upper end of this instrument to drive the prosthesis downwardly as required.

It will also be understood that the procedures described above may be combined, so that initial distraction of the vertebra is achieved by manipulation of the handles 14 and subsequent distraction to the distance necessary to accommodate the prosthesis between them is achieved by tapping or otherwise urging the prosthesis downwardly.

The instrument 10 serves both to facilitate insertion of the prosthesis between the vertebrae and to ensure that the prosthesis is accurately guided into position so that its fins 36 locate properly in the slots 40.

What is claimed is:

1. A method for implanting an intervertebral prosthesis, the method comprising:
   inserting a prosthesis having two vertebral contacting surfaces and at least one fin projecting from at least one of the two vertebral contacting surfaces into a placement instrument comprising opposed jaws, with the at least one fin slidably received in at least one slot in the opposed jaws and the opposed jaws being inclined toward tips of one another to define a gap in the placement instrument opposite the tips for insertion of the prosthesis;
   inserting the tips of the opposed jaws between adjacent vertebrae;
   moving the jaws apart from one another to cause distraction of the vertebrae; and
   implanting the prosthesis by sliding the at least one fin of the prosthesis in the at least one slot of the jaws and guiding the at least one fin of the prosthesis into a vertebral slot cut into at least one of the vertebrae.

2. A method according to claim 1, wherein the step of moving the jaws apart from one another is performed by driving the prosthesis downward in the jaws to force the jaws and the vertebrae apart.

3. A method according to claim 1, wherein the at least one fin comprises a fin on each of the two vertebral contacting surfaces and wherein the at least one slot of the jaws comprises a slot on each of the opposing inner surfaces of the jaws.

4. A method according to claim 1, further comprising an initial step of cutting the vertebral slot into one of the vertebrae.

5. A method for implanting an intervertebral prosthesis, the method comprising:
   providing a placement instrument comprising opposed jaws and at least one slot in the opposed jaws configured to receive at least one fin of a prosthesis, the opposed jaws being inclined toward tips of one another to define a gap in the placement instrument opposite the tips;
   inserting the tips of the opposed jaws between adjacent vertebrae;
   moving the jaws apart from one another to cause distraction of the vertebrae;
   inserting a prosthesis having two vertebral contacting surfaces and the at least one fin projecting from at least one of the two vertebral contacting surfaces into the gap in the placement instrument with the at least one fin of the prosthesis received in the at least one slot of the jaws; and
   implanting the prosthesis by sliding the at least one fin of the prosthesis in the at least one slot of the jaws and guiding the at least one fin of the prosthesis into a vertebral slot cut into one of the vertebrae.

6. A method according to claim 5, wherein the step of moving the jaws apart from one another is performed by manipulation of a pair of handles of the placement instrument.

7. A method according to claim 5, wherein the at least one fin comprises a fin on each of the two vertebral contacting surfaces and wherein the at least one slot of the jaws comprises a slot on each of the opposing inner surfaces of the jaws.

8. A method according to claim 5, further comprising an initial step of cutting the vertebral slot into one of the vertebrae.

9. A method according to claim 1, wherein the at least one slot of the jaws comprises two substantially parallel side walls, wherein the at least one fin comprises two substantially parallel side walls and the spacing of the side walls of the slot of the jaws is configured to fit and guide the at least one fin.

10. A method according to claim 5, wherein the at least one slot of the jaws comprises two substantially parallel side walls, wherein the at least one fin comprises two substantially parallel side walls and the spacing of the side walls of the slot of the jaws is configured to fit and guide the at least one fin.

* * * * *